(12) United States Patent
Galaev et al.

(10) Patent No.: US 11,878,992 B2
(45) Date of Patent: Jan. 23, 2024

(54) CRYSTALLIZATION OF STEVIOL GLYCOSIDES

(71) Applicant: DSM IP Assets B.V., Heerlen (NL)

(72) Inventors: Igor Galaev, Echt (NL); Robertus Mattheus De Pater, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/322,410

(22) PCT Filed: Aug. 9, 2017

(86) PCT No.: PCT/EP2017/070240
§ 371 (c)(1),
(2) Date: Jan. 31, 2019

(87) PCT Pub. No.: WO2018/029272
PCT Pub. Date: Feb. 15, 2018

(65) Prior Publication Data
US 2019/0194240 A1    Jun. 27, 2019

Related U.S. Application Data

(60) Provisional application No. 62/372,733, filed on Aug. 9, 2016.

(51) Int. Cl.
| | | |
|---|---|---|
| *C07H 15/256* | (2006.01) | |
| *C07H 1/06* | (2006.01) | |
| *C12J 1/08* | (2006.01) | |
| *A23F 3/40* | (2006.01) | |
| *A23F 5/46* | (2006.01) | |
| *C12G 3/06* | (2006.01) | |
| *A23L 2/60* | (2006.01) | |
| *C12C 5/02* | (2006.01) | |
| *C07H 1/08* | (2006.01) | |

(52) U.S. Cl.
CPC .......... *C07H 15/256* (2013.01); *A23F 3/405* (2013.01); *A23F 5/465* (2013.01); *A23L 2/60* (2013.01); *C07H 1/06* (2013.01); *C12C 5/026* (2013.01); *C12G 3/06* (2013.01); *C12J 1/08* (2013.01); *C07H 1/08* (2013.01); *C12G 2200/21* (2013.01)

(58) Field of Classification Search
CPC .................. C07H 15/256; C07H 1/08
USPC ......................................... 536/127
See application file for complete search history.

(56) References Cited

U.S. PATENT DOCUMENTS

| | | | |
|---|---|---|---|
| 5,962,678 A | 10/1999 | Payzant et al. | |
| 5,972,120 A * | 10/1999 | Kutowy | A23L 27/36 536/18.1 |
| 6,255,557 B1 * | 7/2001 | Brandle | A01H 5/12 800/260 |
| 8,017,168 B2 * | 9/2011 | Prakash | A23L 2/52 426/534 |
| 2006/0083838 A1 | 4/2006 | Jackson et al. | |
| 2007/0082103 A1 | 4/2007 | Magomet et al. | |
| 2014/0357588 A1 | 12/2014 | Markosyan et al. | |
| 2015/0017284 A1 * | 1/2015 | Prakash | A23L 27/36 426/654 |
| 2016/0153017 A1 * | 6/2016 | Van Der Hoeven | C12N 15/52 536/18.1 |
| 2016/0213039 A1 | 7/2016 | Kumar et al. | |
| 2018/0371003 A1 | 12/2018 | Geertman et al. | |

FOREIGN PATENT DOCUMENTS

| | | |
|---|---|---|
| CN | 102199177 A | 9/2011 |
| CN | 104151378 A | 11/2014 |
| CN | 104163839 A | 11/2014 |
| CN | 104341470 A | 2/2015 |
| CN | 105283464 A | 1/2016 |
| CN | 105408339 A | 3/2016 |
| CN | 105658081 A | 6/2016 |
| CN | 105722533 A | 6/2016 |
| CN | 106866757 A | 6/2017 |
| JP | 5523756 B2 | 6/2014 |
| WO | 2007149672 A2 | 12/2007 |
| WO | WO 2010118218 A1 * | 10/2010 |
| WO | 2011082288 A1 | 7/2011 |
| WO | 2014146135 A2 | 9/2014 |
| WO | WO 2015007748 A1 * | 1/2015 |
| WO | 2015113231 A1 | 8/2015 |
| WO | 2016023103 A1 | 2/2016 |
| WO | 2017009293 A1 | 1/2017 |

OTHER PUBLICATIONS

Das et al. (Separation and Purification Technology 144 (2015) 8-15).*
International Search Report issued in counterpart Application No. PCT/EP2017/070240, dated Oct. 12, 2017.

(Continued)

*Primary Examiner* — Ganapathy Krishnan

(74) *Attorney, Agent, or Firm* — McBee Moore & Vanik, IP, LLC

(57) ABSTRACT

A method for purifying rebaudioside M, which method comprises: (a) providing a solution comprising rebaudioside M at a concentration of at least about 10 g/L and at a purity of at least about 10% by weight on a dry basis; and (b) crystallizing from the solution a high purity composition comprising rebaudioside M, thereby to purify rebaudioside M.

16 Claims, 3 Drawing Sheets

(56) References Cited

OTHER PUBLICATIONS

Humphrey et al., "Spatial organisation of four enzymes from Stevia rebaudiana that are involved in steviol glycoside synthesis" Plant Molecular Biology. (2006) 61: 47-62.
Mohamed et al., "UDP-dependent glycosyltransferases involved in the biosynthesis of steviol glycosides" Journal of Plant Physiology. (2011) vol. 68:1136-1141.
Verduyn et al., "Effect of Benzoic Acid on Metabolic Fluxes in Yeasts: A Continuous-Culture Study on the Regulation of Respiration and Alcoholic Fermentation" Department of Microbiology and Enzymology. Yeast. (1992) vol. 8: 501-517.

* cited by examiner

CRYSTALLIZATION OF STEVIOL GLYCOSIDES

CROSS-REFERENCE TO RELATED APPLICATIONS

This application is a National Stage entry of International Application No. PCT/EP2017/070240, filed 9 Aug. 2017, which claims benefit to U.S. Provisional Application No. 62/372,733, filed 9 Aug. 2016.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-497000_ST25.bd" created on 8 Jan. 2019, and 143,312 bytes in size) is submitted concurrently with the instant application, and the entire contents of the Sequence Listing are incorporated herein by reference.

FIELD

The present invention relates to a method for purifying rebaudioside M and to a composition comprising rebaudioside M obtainable by the method.

BACKGROUND

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Current Joint FAO/WHO Expert Committee on Food Additives (JECFA) standards require that the total amount of steviol glycosides be purified to 95% or greater.

Existing methods for purification of rebaudioside A relies on repeated purification steps including chromatography, a capital expensive and time-consuming operation, and the use of organic solvents. The use of organic solvents requires complex and expensive equipment, as, for example, so-called explosion free equipment must be used. The need to regenerate organic solvents and actions that need to be taken to reduce their environmental impact due to solvent exhaust further add to costs.

Previously reported efforts to purify rebaudioside A from mixtures of rebaudioside A and stevioside require numerous repeated purification steps. U.S. Pat. No. 5,962,678 discloses the re-crystallization of rebaudioside A using an anhydrous methanol solution to obtain an 80% pure rebaudioside A. By repeating the re-crystallization with anhydrous methanol numerous times, the purity of rebaudioside A may be increased to over 95%. U.S. Patent Publication No. 2006/0083838 discloses purification of rebaudioside A through re-crystallization with a solvent comprising ethanol and between 4 and 15% water. Japanese Patent Application No. 55-23756 discloses a method for purifying rebaudioside A and stevioside by crystallization from aqueous ethanol (>70%) to obtain an 80% pure rebaudioside A. U.S. Patent Publication No. 2007/0082103 discloses a method for purifying rebaudioside A by recrystallization from aqueous ethanol, asserting a two-step recrystallization from crude rebaudioside (60%) results in the formation of >98% pure rebaudioside at 97% yield. WO2007/149672 and WO2011/082288 disclose single step crystallization methods using organic solvents.

These prior art methods, however, either do not provide a substantially pure steviol glycoside composition nor a rebaudioside composition of sufficient purity using only a single recrystallization step which is capable of satisfying current JECFA standards and typically require the use of chromatography and of organic solvents. Moreover, such recovery methods have not been reported in relation to purification of rebaudioside M.

Accordingly, there exists a need for a simple, efficient, and economical method for preparing substantially pure steviol glycoside compositions, ideally which reduce the need for chromatography and/or the use of organic solvents.

SUMMARY

The present invention is based on the finding that rebaudioside M (rebM) may be crystallized directly from a water solution comprising that steviol glycoside. This direct crystallization allows a high purity rebM composition, such as a substantially pure composition of rebM, to be achieved potentially in a single unit operation, typically without the need for adsorption chromatography (also referred to as "binding elution chromatography") and/or without the need for use of organic solvents.

Accordingly, the invention addresses the need to provide a method for purifying a steviol glycoside composition comprising rebM to obtain a composition having a higher purity of rebM and, preferably, with a high yield.

According to the invention there is thus provided, a method for purifying rebaudioside M, which method comprises:
   (a) providing a solution comprising rebaudioside M at a concentration of at least about 10 g/L and at a purity of at least about 10% by weight on a dry basis; and
   (b) crystallizing from the solution a high purity composition comprising rebaudioside M, thereby to purify rebaudioside M.

The invention also provides:
   a method for purifying rebaudioside M, which method comprises purifying the rebaudioside M substantially in the absence of an organic solvent;

a method for purifying rebaudioside M, which method comprises purifying the rebaudioside M in the absence of a step of adsorption chromatography; and a composition comprising rebaudioside M obtainable by a method according to any one of the preceding claims.

DETAILED DESCRIPTION

Figure 1:
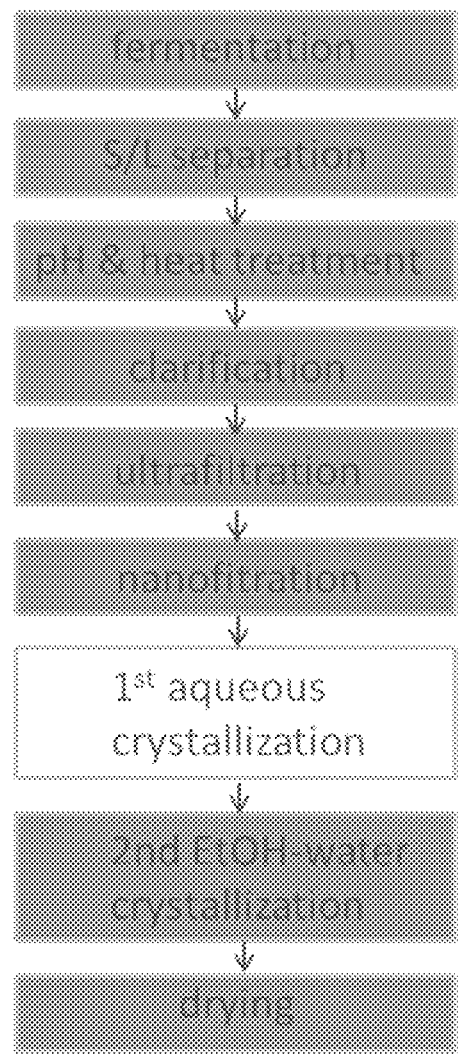
FIG. 1 sets out the direct crystallization recovery process for steviol glycosides.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Steviol glycoside compositions may be used as natural high-potency sweeteners. rebM is one of the steviol glycosides that may be found in varying amounts in steviol glycoside compositions. Typically, rebM is found only in trace amounts in plant-derived extracts, although it may be present at higher amounts in fermentation-derived steviol glycoside compositions.

As the amount of the total rebM in a steviol glycoside composition is increased, the cost of the composition is still further increased.

Accordingly, there exists a need to provide a method for preparing high purity rebM comprising compositions in an economic manner.

In particular, there exists a need to provide a method for preparing substantially pure steviol glycoside compositions having a high purity of rebM in an economic manner.

This invention satisfies this need by providing a method for purifying a lower purity rebM comprising composition to a higher purity rebM comprising composition, for example a substantially pure rebM comprising composition.

Purity, as used herein with respect to a given rebaudioside such as rebM represents the weight percentage of that rebaudioside in a given composition on a dry weight basis.

In the method of the invention, a lower purity solution of rebM is provided that may be directly crystallized to allow a higher purity steviol glycoside composition to be obtained. The method typically does not require the use of adsorption chromatography or the use of organic solvents.

That is to say, the method of the invention is typically one where the high purity rebM comprising composition is obtained from a lower purity rebM comprising composition by direct crystallization of rebM from water.

The invention thus relates to:
a method for purifying rebM, which method comprises purifying the rebM substantially in the absence of an organic solvent; and
a method for purifying rebM, which method comprises purifying the rebM in the absence of a step of adsorption chromatography.

Accordingly, the invention relates to a method for purifying rebaudioside M, which method comprises:
(a) providing a solution comprising rebaudioside M at a concentration of at least about 10 g/L and at a purity of at least 10% by weight on a dry basis; and
(b) crystallizing from the solution a high purity composition comprising rebaudioside M, thereby to purify rebaudioside M.

That is to say, the method method of the invention allows purification of a steviol glycoside composition comprising rebM at a low purity, for example at a purity of at least about 10% rebM by weight on a dry basis (herein "a low purity composition" or "a low purity solution"), such that the resulting steviol glycoside composition comprises rebM at a high purity (herein "a high purity composition"), for example at least about 60% rebM by weight on a dry basis.

FIG. 1 illustrates one way in which the method of the invention may be carried out.

The process may comprise a concentration step. The invention thus relates to a method for purifying rebaudioside M, which method comprises:
(a) providing a solution comprising rebaudioside M at a concentration of at least about 10 g/L and at a purity of at least 10% by weight on a dry basis;
(b) concentrating the said solution to achieve a solution comprising rebaudioside M at a concentration of at least about 80 g/L; and
(c) crystallizing from the solution a high purity composition comprising rebaudioside M,
thereby to purify rebaudioside M.

The concentration of rebM in the low purity solution may be at least about 10 g/L, for example at least about 15 g/L, such as at least about 30 g/L, such as at least about 40 g/L.

The solution in step (a) may be concentrated so that the rebM concentration in the solution is increased to at least about 50 g/L, at least about 100 g/L, at least about 150 g/L, at least about 200 g/L, at least about 250 g/L or at least about 300 g/L or higher.

The solution in step (a) may have a purity of rebM of at least about 10% by weight on a dry weight basis, for example at least about 15% on a dry weight basis, for example at least about 20% on a dry weight basis, for example at least about 30% on a dry weight basis, for example at least about 40% on a dry weight basis, such as at least about 50% on a dry weight basis or higher.

Any combination of the concentrations and purities mentioned above may be used to define a suitable low purity solution for use in the method.

For example, the solution in step (a) may have a concentration of rebM of 10 g/L and a purity of 15% or 20% on a dry weight basis.

The solution in step (a) may be a crude steviol glycoside composition in its raw form, as extracted from *Stevia* plants. Alternatively, the solution may comprise steviol glycosides formed by enzymatic conversion of steviol or steviol glycosides. Preferably though, such a solution is a fermentatively-produced steviol glycoside composition. That is to say, the solution may be a composition comprising steviol glycosides produced by fermentation.

Accordingly, the solution in step (a) which comprises rebM may be one obtained from the *Stevia rebaudiana* plant or by enzymatic conversion of steviol and/or steviol glycosides. Preferably, however, such a solution may be one derived from the fermentative production of steviol glycosides (see, for example, WO2015/007748).

Thus, the solution in step (a) which comprises rebM may be a fermentation broth or may be one derived from a fermentation broth, i.e. produced by an organism capable of converting a carbon source into rebM.

If a fermentatively-produced steviol glycoside composition comprising rebM is used, one or more recovery steps may be carried out in order to provide the solution comprising rebM in step (a). For example, a solid-liquid separation step, for example by centrifugation, may be used to separate cells from the broth. Optionally, solid-liquid separation may be followed by a clarification step.

The solution comprising rebM may be provided such that the concentration of rebM is less than about 10 g/L and subsequently concentrated to provide the solution comprising rebM at a concentration of at least about 10 g/L. Suitable concentration techniques are described herein.

The solution comprising rebM in step (a) generally comprises other steviol glycosides and impurities. RebM may represent up to about 70 to 75% of the total steviol glycosides. Other impurities, such as non-digested sugars, proteins and salts may comprise about 50% to about 60% of total dry matter.

The method of the invention may result in the preparation of a high purity composition comprising rebM in a purity of at least about 60% by weight on a dry basis, for example at least about 70% by weight on a dry basis, for example at least about 80% or more by weight on a dry basis, for example at least about 90% or more by weight on a dry basis, for example at least about 95% or more by weight on a dry basis or even higher purity.

A substantially pure composition comprising rebM may comprise rebM at a purity of at least about 95% by weight on a dry basis, for example at least about 98%, such as at least about 95% or more by weight on a dry basis or even higher purity.

In the method of the invention, the high purity composition comprising rebM may comprise one or more further steviol glycosides. Accordingly, the high puritiy composition comprising rebM may comprise rebM at an amount of at least about 70% by weight rebM on a dry basis, for example at least about 80% or more by weight on a dry basis, for example at least about 90% or more by weight on a dry basis, for example at least about 95% or at least about 98% by weight on a dry basis of total steviol glycosides.

The high purity composition comprising rebM which is produced according to the method of the invention typically may comprise no more than about 150 ppm on a dry weight basis of kaurenoic acid and/or kaurenoic acid equivalents, for example no more than about 100 ppm on a dry weight basis of kaurenoic acid and/or kaurenoic acid equivalents, such as no more than about 50 ppm on a dry weight basis of kaurenoic acid and/or kaurenoic acid equivalents.

The high purity composition comprising rebM which is produced according to the method of the invention typically may comprise no more than about 2% on a dry weight basis of stevioside.

Concentration, if used, may be carried out by any convenient method. Typically, any concentrating step does not comprise chromatography to concentrate the amount of the desired steviol glycoside. That is to say, the method of the invention is typically one in which adsorption chromatography is not used, i.e. is one where there is no step of adsorption chromatography. Adsorption chromatography is sometimes referred to as binding elution chromatography.

The concentrating step, if used, may comprise:
a combination of ultrafiltration and nanofiltration;
evaporation;
and/or spray-drying the solution in step (a) and then redissolving the spray-dried material.

A concentration step (may comprise (i) ultrafiltration and nanofiltration; and/or (ii) evaporation, for example a combination of ultrafiltration and nanofilteration, followed by evaporation.

Ultrafiltration may be carried out with a membrane with a membrane having a cut-off of from about 3 kDa to about 15 kDa, for example about 10 kDa.

Nanofiltration may be carried out with a membrane with a membrane having a nominal retention of sodium sulphate above 90%.

In the method of the invention the high purity composition comprising rebM is may preferably be crystallized from a water solution. That is to say, the high purity composition comprising rebM may be crystallized from an aqueous solution comprising rebM at a lower purity. For the purposes of the invention, an aqueous solution is one which comprises substantially no organic solvent. Thus, an aqueous solution may be one where substantially the only solvent is water (i.e low or trace amounts of other solvents may be present, for example about 2% or less organic solvent(s), such as about 1% or less organic solvent(s)).

The crystallization may be a single step crystallization.

Thus, the method of the invention may be carried out substantially in the absence of organic solvent.

In the method of the invention, the solution in step (a) or the concentrated solution (if a concentration step is used) may be seeded with an amount of rebM sufficient to promote crystallization of the rebM.

The method of the invention may comprise separating and washing the high purity composition comprising rebM. Such steps may be carried out substantially in the absence of any organic solvent.

The method of the invention may comprise drying the high purity composition comprising rebM.

The method of the invention may comprise one or more further purification crystallization steps (for example polish crystallization) to remove additional impurities. Such additional steps may be carried out using water or in the presence of one or more organic solvent.

The method of the invention may thus be one in which all crystallization steps are carried out substantially in the absence of any organic solvent.

A preferred method of the invention is one in which no adsorption chromatography step is used and wherein the crystallization step or crystallization steps are carried out substantially in the absence of any organic solvent, for example in water. In such a method, there may be no use of organic solvent at all, for example in any separating or washing steps, where water may be used.

The make-up and yield of the resulting high purity composition comprising rebM may be controlled through the appropriate selection of parameters such as the manner in which concentration is carried out (if such a step is used), the solution temperature, the precipitation temperature, the mixing time, the precipitation time, the pH and seeding of the solution.

The method of crystallizing the low purity solution or a concentrated form of that solution may be carried out at any suitable temperature. Such temperatures generally may range from about 20° C. to about 85° C., for example at about 75° C.

In particular, the crystallization of the low purity solution or a concentrated form of that solution may further comprise cooling the said low purity solution or concentrate. Generally, the low purity solution or concentrate may be cooled to a temperature suitable for precipitation ("precipitation temperature") of rebM.

Examples of such precipitation temperatures may be in a range from about 4° C. to about 65° C., from about 15° C. to about 45° C., or any temperature there between.

Crystallization of the low purity steviol glycoside solution may be allowed to take place for a length of time sufficient ("precipitation time" or "cooling time") to obtain a desirable yield of the substantially pure steviol glycoside composition from the low purity steviol glycoside solution. For example, in particular embodiments the crystallization of the low purity steviol glycoside solution may proceed from about 0.5 hours to about 120 hours (5 days), about 12 hours to about 96 hours (4 days), about 24 hours (1 day) to about 72 hours (3 days), for about 48 hours (2 days), or for any length of time therebetween.

After crystallization, a higher purity rebM comprising composition, for example a substantially pure rebM comprising composition may be obtained.

The total yield of the higher purity steviol glycoside composition may be at least about 20%, for example at least about 25%, such at least about 30%. Yield is used herein generally to refer to the mass obtained relative to the starting mass.

The method of the invention may further comprise seeding the low purity steviol glycoside solution upon beginning the crystallization of the low purity steviol glycoside solution. Seeding generally may be performed at the same temperature at which the crystallization is allowed to proceed. For example, the seeding will be conducted at temperatures in the range of about 20° C. to about 85° C., such as at a temperature of about 75° C.

Seeding of the low purity steviol glycoside solution generally may be performed by adding substantially pure crystals of rebM to the low purity solution or concentrate in an amount sufficient to promote precipitation of rebM.

The method of the invention may further comprise separating and washing the higher purity steviol glycoside composition after its crystallization. The higher purity steviol glycoside composition may be separated from its supernatant (the organic solvent and impurities) by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any pressure, vacuum, or gravity filtration methods, that include without limitation, the use of belt, drum, nutsche type, leaf, plate, Rosenmund type, sparkler type, and bag filters and filter press. Operation of the solid-liquid separation device may be continuous, semi-continuous or in batch mode. The higher purity steviol glycoside composition also may be washed on the separation device using water, various organic solvents and mixtures thereof and can be partially or totally dried on the separation device using any number of gases, including, without limitation, nitrogen or argon, to evaporate residual liquid. The higher purity steviol glycoside composition may be automatically or manually removed from the separation device using liquids, gases or mechanical means by either dissolving the solid or maintaining the solid form.

The method of the invention may further comprise drying the higher purity steviol glycoside composition. Suitable methods for drying such compositions are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the higher purity steviol glycoside composition is dried using a nitrogen or argon purge to remove the residual solvent at a temperature in a range from about 40° C. to about 60° C. for a period of time from about 5 hours to about 5 days, from about 1 day to about 4 days, from about 2 days to about 3 days, or for any length of time there between.

If further purification is desired, the method of purifying the low purity solution may be repeated or the higher purity composition may be further purified, for example, by ion exchange chromatography.

The total steviol glycosides generally comprise one or more of steviol glycosides selected from the group consisting of rebaudioside A, rebaudioside B, rebaudioside C, rebaudioside D, rebaudioside F, stevioside, dulcoside A, rubusoside, and steviolbioside.

The purity of the composition may be measured using methods known to those of ordinary skill in the art. One such method includes high performance liquid chromatography (HPLC). Those of ordinary skill in the art also should appreciate that the moisture in the sample may affect the accuracy of purity measurements. Accordingly, the composition should be substantially dry when measured for purity. As used herein, a "substantially dry composition" and "on a dry basis" are used interchangeably and may comprise up to about 10% by weight of moisture.

The rebM solution used in the invention may be fermentatively-produced, for example may be a fermentation broth or a solution derived from a fermentation broth. Such a rebM solution may be derived from a recombinant host capable of producing a steviol glycoside.

Accordingly, a suitable recombinant host may be capable of producing rebM.

A suitable recombinant host may comprise one or more recombinant nucleic acid sequences encoding one or more polypeptides having UDP-glycosyltransferase (UGT) activity.

For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Figure 2:
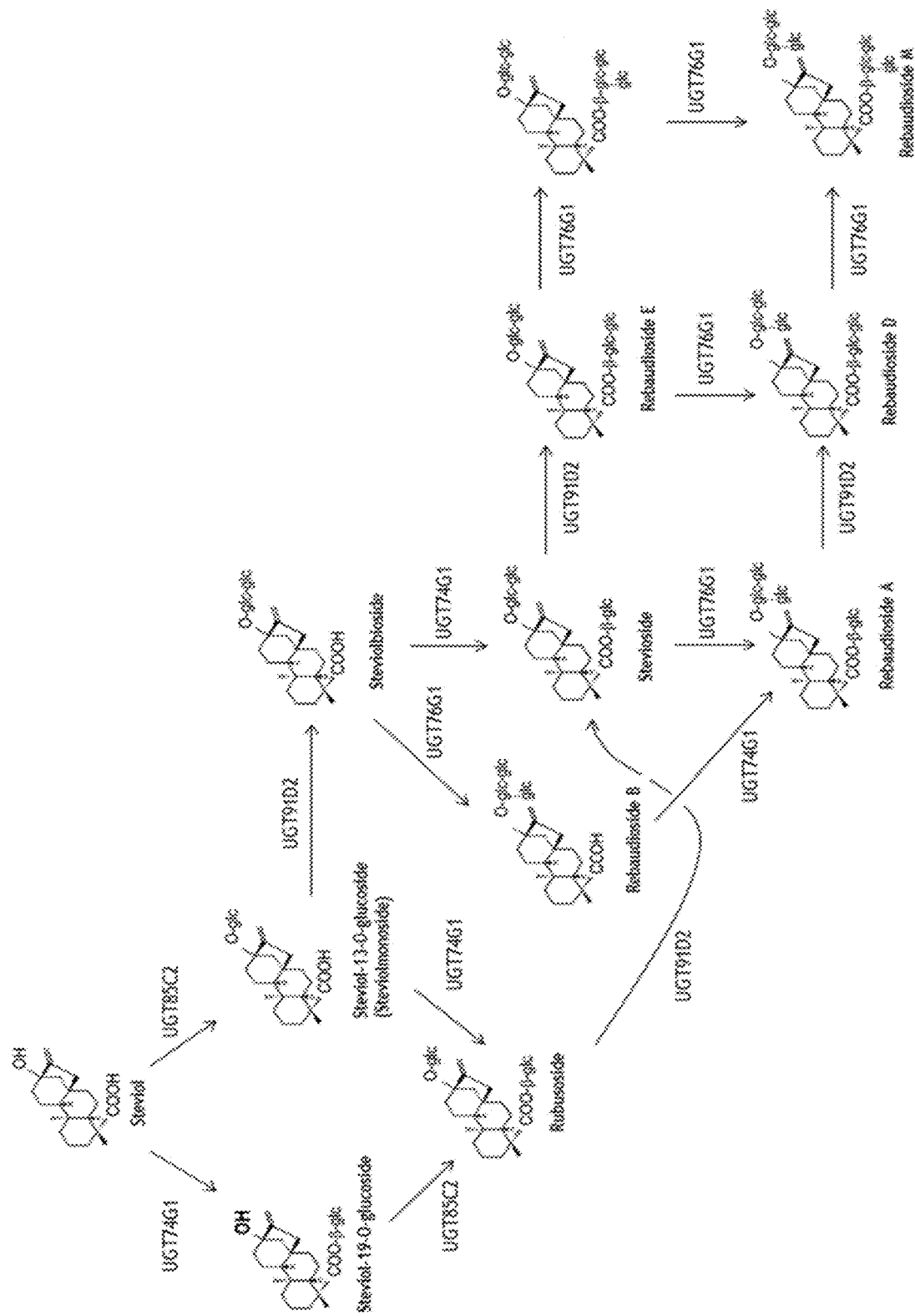
FIGS. 2 and 3 set out schematic diagrams of the potential pathways leading to biosynthesis of steviol glycosides.
Figure 3:
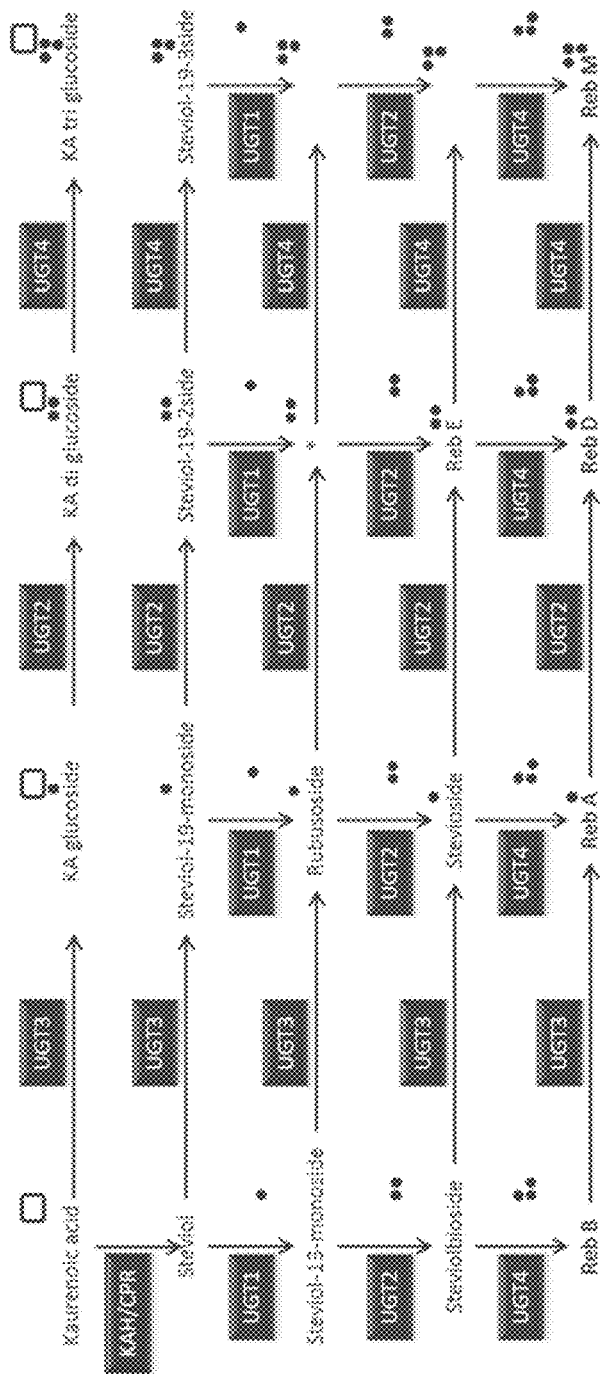

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIGS. 2 and 3 set out schematic diagrams of steviol glycoside formation.

A recombinant host may thus comprise one or more recombinant nucleic acid sequences encoding one or more of:
 (i) a polypeptide having UGT74G1 activity;
 (ii) a polypeptide having UGT2 activity;
 (ii) a polypeptide having UGT85C2 activity; and
 (iii) a polypeptide having UGT76G1 activity.

A recombinant host may comprise a nucleotide sequence encoding a polypeptide capable of catalyzing the addition of a C-13-glucose to steviol. That is to say, a recombinant yeast suitable for use in a method of the invention may comprise a UGT which is capable of catalyzing a reaction in which steviol is converted to steviolmonoside.

Such a recombinant host may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-O-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant host may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-O-glucoside transferase, transferring a rhamnose moiety to the C-2' of the 13-O-glucose of the acceptor molecule, steviol.

A recombinant host may comprise a nucleotide sequence encoding a polypeptide having UGT activity may comprise a nucleotide sequence encoding a polypeptide capable of catalyzing the addition of a C-19-glucose to steviolbioside. That is to say, a recombinant host may comprise a UGT which is capable of catalyzing a reaction in which steviolbioside is converted to stevioside. Accordingly, such a recombinant host may be capable of converting steviolbioside to stevioside. Expression of such a nucleotide sequence may confer on the recombinant yeast the ability to produce at least stevioside.

A recombinant host may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH or the 19-COOH, respectively, of steviol. A suitable UGT74G1 polypeptide may function as a uridine 5'-diphospho glucosyl: steviol 19-COOH transferase and a uridine 5'-diphospho glucosyl: steviol-13-0-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant host may comprise a nucleotide sequence encoding a polypeptide capable of catalyzing glucosylation of the C-3' of the glucose at the C-13 position of stevioside. That is to say, a recombinant yeast suitable for use in a method of the invention may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant host may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-O-1,2 glucoside C-3 ' glucosyl transferase and a uridine 5'-diphospho glucosyl: steviol-19-O-glucose, 13-O-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant host typically comprises nucleotide sequences encoding at least one polypeptide having UGT1 activity, at least one polypeptide having UGT2 activity, least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid encode for a polypeptide which has two, three or four of the activities set out above. Preferably, a recombinant yeast for use in the method of the invention comprises UGT1, UGT2 and UGT3 and UGT4 activity. Suitable UGT1, UGT2, UGT3 and UGT4 sequences are described in Table 1 of WO2015/007748.

A recombinant host may comprise two or more nucleic acid sequences encoding a polypeptide having any one UGT activity, for example UGT1, 2, 3 or 4, activity. Where a recombinant host comprises two or more nucleic acid sequence encoding a polypeptide having any one UGT activity, those nucleic acid sequences may be the same or different and/or may encode the same or different polypeptides. In particular, a recombinant host may comprise a nucleic acid sequence encoding a two different UGT2 polypeptides.

A recombinant host may comprise one or more recombinant nucleotide sequence(s) encoding one of more of:

a polypeptide having ent-copalyl pyrophosphate synthase activity;

a polypeptide having ent-Kaurene synthase activity;

a polypeptide having ent-Kaurene oxidase activity; and a polypeptide having kaurenoic acid 13-hydroxylase activity. For the purposes of this invention, a polypeptide having ent-copalyl pyrophosphate synthase (EC 5.5.1.13) is capable of catalyzing the chemical reaction:

kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

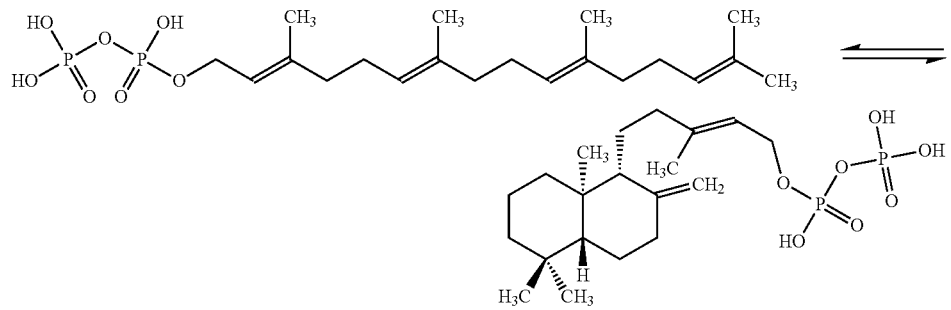

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

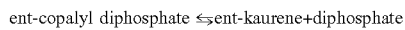

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant host of the invention may encode a polypeptide having ent-copalyl pyrophosphate synthase activity and ent- Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and 02. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

In a recombinant host, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of a host confer(s) on that host the ability to produce elevated levels of GGPP. Thus, a recombinant host according to the invention may comprise one or more recombinant nucleic acid sequence(s)

encoding one or more of hydroxymethylglutaryl-CoA reductase, farnesyl-pyrophosphate synthetase and geranylgeranyl diphosphate synthase.

Accordingly, a recombinant host may comprise nucleic acid sequences encoding one or more of:
- a polypeptide having hydroxymethylglutaryl-CoA reductase activity;
- a polypeptide having farnesyl-pyrophosphate synthetase activity; and
- A recombinant host may be, for example, an multicellular organism or a cell thereof or a unicellular organism. A host may be a prokaryotic, archaebacterial or eukaryotic host cell.
- A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision Eumycotina (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision Eumycotina and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete* Podospora, Pycnoporus, *Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora* thermophyla. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), Brettanomyces, *Kluyveromyces, Candida* (e.g., *C. krusei, C. revkaufi, C. pulcherrima, C. tropicalis, C. utilis*), Issatchenkia (eg. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), Yamadazyma. Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, StbI2, DH5-alpha, DB3, DB3.1), DB4, DB5, JDP682 and ccdA-over (e.g., U.S. application Ser. No. 09/518,188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., Choroflexus bacteria (e.g., *C. aurantiacus*), Chloronema (e.g., *C. gigateum*)), green sulfur bacteria (e.g., *Chlorobium* bacteria (e.g., *C. limicola*), Pelodictyon (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and Rhodomicrobium bacteria (e.g., *R. vanellii*)).

Host Cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and Trichoplusa (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

A recombinant host may be able to grow on any suitable carbon source known in the art and convert it to a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Standard genetic techniques, for the construction of such recombinant hosts, such as overexpression of enzymes in the host cells, genetic modification of host cells, or hybridisation techniques, are known methods in the art, such as described in Sambrook and Russel (2001) "Molecular Cloning: A Laboratory Manual (3$^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265, 186.

A process for the preparation of a steviol glycoside may comprise fermenting a recombinant host as described herein which is capable of producing at least one steviol glycoside in a suitable fermentation medium, and optionally recovering the steviol glycoside.

The fermentation medium used in the process for the production of a steviol glycoside may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as ureum, or an ammonium salt such as ammonium sulphate, ammonium chloride, ammoniumnitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobic, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used.

The production of a steviol glycoside in the process may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present invention may be carried out at any suitable pH value. If the recombinant host is a yeast, the pH in the fermentation medium preferably has a value of below 6, preferably below 5,5, preferably below 5, preferably below 4,5, preferably below 4, preferably below pH 3,5 or below pH 3,0, or below pH 2,5, preferably above pH 2. An advantage of carrying out the fermentation at these low pH values is that growth of contaminant bacteria in the fermentation medium may be prevented.

Such a process may be carried out on an industrial scale. The product of such a process is a fermentation broth comprising one or more steviol glycosides, in particular at least rebM. The broth may then be treated according the method as described herein.

The invention also relates to a composition comprising rebaudioside M obtainable by a method according to the invention (a "composition of the invention").

A composition of the invention may be used in any application known for such compounds. In particular, such a composition may for instance be used as a sweetener, for example in a food or a beverage. According to the invention therefore, there is provided a foodstuff, feed or beverage which comprises a composition of the invention.

For example a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a composition of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A composition of the invention can be used in dry or liquid forms. It can be added before or after heat treatment of food products. The amount of the sweetener depends on the purpose of usage. It can be added alone or in the combination with other compounds.

A composition of the invention may be blended with one or more further non-caloric or caloric sweeteners. Such blending may be used to improve flavour or temporal profile or stability. A wide range of both non-caloric and caloric sweeteners may be suitable for blending with a composition of the invention. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the invention include sugar alcohols and carbohydrates such as sucrose, glucose, fructose and HFCS. Sweet tasting amino acids such as glycine, alanine or serine may also be used.

A composition of the invention can be used in the combination with a sweetener suppressor, such as a natural sweetener suppressor. It may be combined with an umami taste enhancer, such as an amino acid or a salt thereof.

A composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a composition of the invention may be used as a sweetener not only for drinks, foodstuffs, and other products dedicated for human consumption, but also in animal feed and fodder with improved characteristics.

The examples of products where a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions which incorporate a composition of the invention can be made by any method known to those skilled in the art that provide homogenous even or homogeneous mixtures of the ingredients. These methods include dry blending, spray drying, agglomeration, wet granulation, compaction, co-crystallization and the like.

In solid form a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

A composition of the invention may include various bulking agents, functional ingredients, colorants, flavors.

Embodiments of the Invention

1. A method for purifying rebaudioside M, which method comprises:
   (a) providing a solution comprising rebaudioside M at a concentration of at least about 10 g/L and at a purity of at least about 10% by weight on a dry basis; and
   (b) crystallizing from the solution a high purity composition comprising rebaudioside M, thereby to purify rebaudioside M.

2. A method for purifying rebaudioside M according to claim 1, which method comprises:
   (a) providing a solution comprising rebaudioside M at a concentration of at least about 10 g/L and at a purity of at least 10% by weight on a dry basis;
   (b) concentrating the said solution to achieve a solution comprising rebaudioside M at a concentration of at least about 80 g/L; and
   (c) crystallizing from the solution a high purity composition comprising rebaudioside M, thereby to purify rebaudioside M.

3. A method according to embodiment 1 or 2, wherein the high purity composition comprising rebaudioside M comprises rebaudioside M in a purity greater than about 60% by weight on a dry basis.

4. A method according to embodiment 3, wherein the high purity composition comprising rebaudioside M comprises rebaudioside M in a purity greater than about 90% by weight on a dry basis.

5. A method according to any one of the preceding embodiments, wherein the high purity composition comprising rebaudioside M comprises at least about 98% by weight on a dry basis of total steviol glycosides.

6. A method according to any one of the preceding embodiments, wherein the high purity composition comprising rebaudioside M comprises no more than about 150 ppm on a dry weight basis of kaurenoic acid equivalents.

7. A method according to any one of the preceding embodiments, wherein the high purity composition comprises no more than about 2% on a dry weight basis of stevioside.

8. A method according to any one of the preceding embodiments, wherein the concentrating step (b) does not comprise chromatography to concentrate the amount of the desired steviol glycoside.

9. A method according to any one of embodiments 2 to 8, wherein the concentrating step (b) comprises:
a combination of ultrafiltration and nanofiltration;
evaporation;
and/or spray-drying the solution in step (a) and then redissolving the spray-dried material.

10. A method according to any one of the preceding embodiments which is carried out in substantially in the absence of an organic solvent.

11. A method according to any one of the preceding embodiments, wherein the high purity composition comprising rebM is crystallized from a water solution.

12. A method according to any one of the preceding embodiments, further comprising seeding the solution comprising rebaudioside M with an amount of rebaudioside M sufficient to promote crystallization of the rebaudioside M.

13. A method according to any one of the preceding embodiments, further comprising separating and washing the high purity composition comprising rebaudioside M.

14. A method according to any one of the preceding embodiments, further comprising drying the high purity composition comprising rebaudioside M.

15. A method according to any one of the preceding embodiments, wherein a further purification crystallization is carried out.

16. A method according to any one of the preceding embodiments, wherein the rebaudioside M solution comprises fermentatively-produced rebaudioside M.

17. A method for purifying rebaudioside M, which method comprises purifying the rebaudioside M substantially in the absence of an organic solvent.

18. A method for purifying rebaudioside M, which method comprises purifying the rebaudioside M in the absence of a step of adsorption chromatography.

19. A method according to any one of the preceding embodiments, wherein the solution comprising rebaudioside M in (a) has a concentration of rebaudioside M of at least about 15 g/L, at least about 20 g/L, at least about 25 g/L, at least about 30 g/L or at least about 40 g/L.

20. A method according to any one of the preceding embodiments, wherein the solution comprising rebaudioside M in (a) has a purity of rebM of at least about 15% by weight on a dry basis, at least about 20% by weight on a dry basis, at least about 25% by weight on a dry basis, at least about 30% on a dry weight basis, at least about 40% on a dry weight basis or at least about 50% on a dry weight basis or higher.

21. A composition comprising rebaudioside M obtainable by a method according to any one of the preceding embodiments.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Example 1. Direct Crystallization of Rebaudioside M from an Aqueous Stream

*Yarrowia lipolytica* strain STV2216 having the genotype set out in Table 1 was constructed using the approach described in WO2013/110673 and WO2015/007748.

TABLE 1

Genotype of strain STV2216. Between brackets indicates the gene copy number present in the strain

| Strain name | genotype |
|---|---|
| STV2216 | MATB tHMG (2; SEQ ID NO: 39 from WO2017/) GGS (2; SEQ ID NO: 40 from co-pending US62/237,203) CarG (1; SEQ ID NO: 41 from co-pending US62/237,203) CPS (5; SEQ ID NO: 42 from co-pending US62/237,203) KS (4; SEQ ID NO: 43 from co-pending US62/237,203) KO (3; SEQ ID NO: 44 from co-pending US62/237,203) KAH4 (4; SEQ ID NO: 2 from co-pending US62/237,203) KAH4_m4 (1; SEQ ID NO: 4) CPR (45; SEQ ID NO: 11 from co-pending US62/237,203) UGT1 (4; SEQ ID NO: 46) UGT2 (2; SEQ ID NO: 47) UGT3 (2; SEQ ID NO: 48) UGT4 (4; SEQ ID NO: 49) RT18 (1; nucleic acid sequence encoding SEQ ID NO: 4 from co-pending WO2016//151046) |

The *Yarrowia lipolytica* strain was cultivated in shake-flasks containing a medium containing 1% yeast extract and 3.6% glycerol for 1 day at 30° C. and 220 rpm.

Subsequently, a seed fermenter was inoculated with the shake flask preculture. The mineral medium of seed fermentation was based on Verduyn et al. (Verduyn C, Postma E, Scheffers W A, Van Dijken J P. Yeast, 1992 July; 8(7):501-517). The pH was controlled at 5.0 by addition of ammonia (10 wt %). Temperature was controlled at 30° C. $pO_2$ was controlled at 20% by adjusting the stirrer speed.

A production fermenter was inoculated from the seed fermenter after 2 days. The mineral medium of production fermentation was based on Verduyn et al. (Verduyn C, Postma E, Scheffers W A, Van Dijken J P. Yeast, 1992 July; 8(7):501-517). After the batch phase, a glucose feed was started and the glucose concentration in the broth was kept limited. The pH was controlled at 5.7 by addition of ammonia (10 wt %). Temperature was controlled at 30° C. $pO_2$ was controlled at 20% by adjusting the stirrer speed.

Broth samples were diluted in water and 33% acetonitrile and analyzed with LC/MS. The composition of steviol glycosides (SGs) and kaurenoic acid glycosides (KAGs) in the resulting broth is set out in Table 2.

TABLE 2

Composition of fermentation broth

| Compound | Amount (g/kg) |
|---|---|
| RebA | 6.7 |
| RebB | 0.3 |
| RebD | 0.5 |
| Steviol | <LOD |
| Stevioside | 0.2 |
| Kaurenoic acid | <LOD |
| Steviolbioside | <LOD |
| Steviol13monoside | 0.2 |
| Steviol19monoside | <LOD |
| Rubusoside | 0.4 |
| Kaurenoic acid 19 monoglucoside | <LOD |
| Kaurenoic acid 19 diglucoside | <LOD |
| Kaurenoic acid 19 triglucoside | 0.2 |
| Kaurenoic acid 19 tetraglucoside | <LOD |
| RebM | 6.9 |

The fermentation broth after laboratory scale fermentations was processed as follows:
centrifugation 30 min at 4000×g;
pH in the supernatant was adjusted to 3.5 and supernatant was heated 30 min at 70° C.;
the heated supernatant was clarified by centrifugation;
the clarified supernatant was ultrafiltrated through a membrane with 10 kDa cut-off; and
the permeate after ultrafiltration was nanofiltrated using a membrane with 150-300 Da cut-off.

The crystallization of rebaudioside M was observed to begin spontaneously as soon as the concentration of rebaudioside M in the retentate of nanofiltration exceeded 30 g/l. The crystallization was allowed to proceed overnight, the crystals were separated by vacuum filtration and the crystal cake was washed with 2 cake volumes of water and dried in the vacuum oven. Finally, 14.5 g of dried crystals were isolated out of 0.871 kg NF retentate.

The composition of the crystals is presented in the Table 3 below.

TABLE 3

Composition of rebaudioside M crystals

| Component | Unit | Value |
|---|---|---|
| Ash | (%) | 0.09 |
| Reb A | (%) | 4.8 |
| Reb B | (%) | 0.6 |
| Reb C | (%) | <LOD |
| Reb D | (%) | 0.5 |
| Reb E | (%) | <LOD |
| Reb M | (%) | 95 |
| Stevioside | (%) | 0.037 |
| Steviolbioside | (%) | 0.01 |
| Rebaudioside G | (%) | <LOD |
| Rubusoside | (%) | 0.01 |
| Steviol19monoside | (%) | 0.0008 |
| Steviol13monoside | (%) | 0.01 |
| Steviol | (ppm) | 4 |
| Isosteviol | (ppm) | <LOD |
| Kaurenoic acid | (ppm) | <LOD |
| Kaurenoic acid 19 monoglucoside | (ppm) | <LOD |
| Kaurenoic acid 19 diglucoside | (ppm) | <LOD |
| Kaurenoic acid 19 triglucoside | (ppm) | <LOQ |
| Kaurenoic acid 19 tetraglucoside | (ppm) | <LOD |

To achieve further purification from KAGs, the crystals produced from the fermentation broth were re-crystallized from aqueous solution as following.

The suspension of 2.5 g crystals in 100 ml water was heated to 75° C. for 10 minutes to dissolve the crystals. The solution was cooled to 20° C. at 10° C./h and incubated at this temperature overnight. The crystals formed were filtered by vacuum and washed with two cake volumes of 95% ethanol The choice of washing liquid was because of the low rebaudioside M solubility in it. The crystals were dried at 60° C. under vacuum overnight. The procedure resulted in 1.7 g of dry Reb-M crystals. The crystals contained >95% Reb-M as determined by LC-UV and the level of all KAG was below the limit of detection of LC-MS.

The invention claimed is:

1. A method for purifying rebaudioside M, which method comprises:
    (a) providing a solution comprising rebaudioside M, wherein the solution is a fermentation broth which has undergone a solid-liquid separation to separate cells from the fermentation broth, wherein the rebaudioside M in the solution has a concentration of at least about 10 g/L and a purity of at least 10% by weight on a dry basis; and
    (b) crystallizing rebaudioside M from the solution of (a) wherein the crystallizing is carried out in water and in the absence of organic solvent, thereby obtaining purified rebaudioside M,
wherein the method is performed without chromatography, and in the absence of organic solvent.

2. The method according to claim 1, wherein the purified rebaudioside M has a purity greater than about 90% by weight on a dry basis.

3. The method according to claim 1, wherein the purified rebaudioside M has a purity of at least about 98% by weight on a dry basis of total steviol glycosides.

4. The method according to claim 1, wherein the purified rebaudioside M comprises no more than about 150 ppm of kaurenoic acid equivalents on a dry weight basis.

5. The method according to claim 1, wherein the purified rebaudioside M comprises no more than about 2% stevioside by weight on a dry weight basis.

6. The method according to claim 1, wherein the purified rebaudioside M has a purity greater than about 60% by weight on a dry basis.

7. The method according to claim 1, further comprising, before (b), seeding the solution with an amount of rebaudioside M crystals sufficient to promote crystallization of the rebaudioside M.

8. The method according to claim 1, further comprising separating and washing the purified rebaudioside M.

9. The method according to claim 1, further comprising drying the purified rebaudioside M.

10. The method according to claim 1, wherein the purified rebaudioside M is subjected to a second purification recrystallization in water.

11. The method according to claim 1, wherein the solution comprising rebaudioside M of (a) has a concentration of rebaudioside M of at least 15% on a dry weight basis.

12. The method according to claim 1, wherein the solution comprising rebaudioside M of (a) has a concentration of rebaudioside M of at least 15 g/L.

13. The method of claim 1, wherein (a) further comprises concentrating the solution comprising rebaudioside M, to yield a concentrated solution.

14. The method of claim 13, wherein the concentrated solution comprises rebaudioside M at a concentration of at least 30 g/L.

15. The method of claim 13, wherein the concentrated solution comprises rebaudioside M at a concentration of at least 80 g/L.

16. The method of claim 13, wherein the concentrating comprises:
   a combination of ultrafiltration and nanofiltration;
   evaporation; and/or
   spray-drying the solution of (a) and then redissolving the spray-dried material.

* * * * *